United States Patent [19]

Skakoon et al.

[11] Patent Number: 4,844,397
[45] Date of Patent: Jul. 4, 1989

[54] INTRAVENOUS POLE CLAMP

[75] Inventors: James G. Skakoon, Melrose; Thomas Chan, Medford, both of Mass.

[73] Assignee: C. R. Bard, Inc., Murray Hill, N.J.

[21] Appl. No.: 211,774

[22] Filed: Jun. 27, 1988

[51] Int. Cl.[4] ............................................. F16M 13/00
[52] U.S. Cl. ................................. 248/231.7; 269/249; 70/19; 70/230
[58] Field of Search ...................... 248/74.4, 121, 122, 248/125, 218.4, 230, 231.6, 231.7, 316.1, 316.6; 24/486, 514, 525; 70/19, 229, 230, 231; 269/249; 411/246, 250, 251, 252, 6

[56] References Cited

U.S. PATENT DOCUMENTS

| | | | |
|---|---|---|---|
| D. 269,156 | 5/1983 | Slinkard . | |
| 1,161,647 | 11/1915 | Finkbeiner | 411/252 |
| 1,549,567 | 8/1925 | Baldwin | 269/249 |
| 1,565,253 | 12/1925 | Butters | 70/230 |
| 1,819,813 | 8/1931 | Ellenberger | 70/19 |
| 2,478,339 | 8/1949 | Sullivan | 70/230 |
| 2,711,300 | 6/1955 | Nelson | 248/230 |
| 4,231,240 | 11/1980 | Fujita | 70/231 |
| 4,321,992 | 3/1982 | Gallo . | |
| 4,515,278 | 5/1985 | DeVroom | 248/231.7 |
| 4,572,536 | 2/1986 | Doughty . | |
| 4,586,691 | 5/1986 | Kozlow . | |
| 4,666,111 | 5/1987 | Schuler | 248/231.7 |
| 4,742,981 | 5/1988 | Converse | 248/231.7 |

Primary Examiner—Ramon O. Ramirez
Assistant Examiner—Robert A. Olson
Attorney, Agent, or Firm—Kane, Dalsimer, Sullivan, Kurucz, Levy, Eisele and Richard

[57] ABSTRACT

An intravenous pole clamp contains a locking mechanism which employs a spring clutch. The clamp body has an attachment for a medical device and a chamber for receiving an I-V pole. A threaded stud is rotated inwardly to clamp the I-V pole. A spring having one fixed end and one free end is threaded onto the shaft of the threaded stud. A locking mechanism allows the free end of the spring to be unrestrained in a locked position. When unlocked, a pin of the locking mechanism slightly unwinds and restrains the free end of the spring freeing the threaded stud to rotate in either an inward or an outward direction. In a locked position, the threaded stud can rotate inwardly but if it is attempted to rotate it outwardly the spring clutches the threaded stud preventing outward rotation.

9 Claims, 4 Drawing Sheets

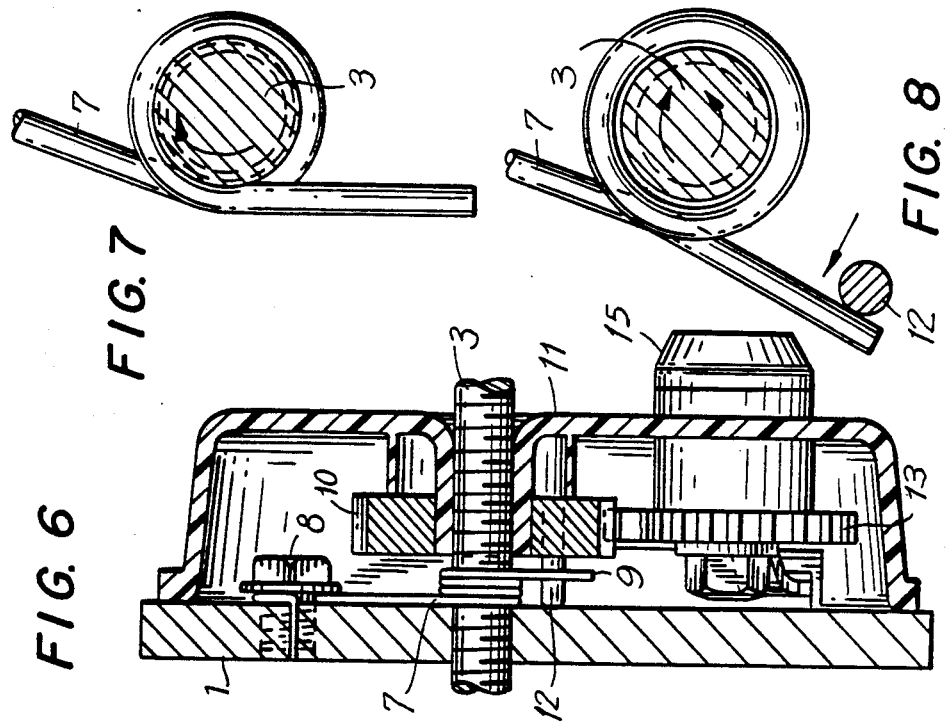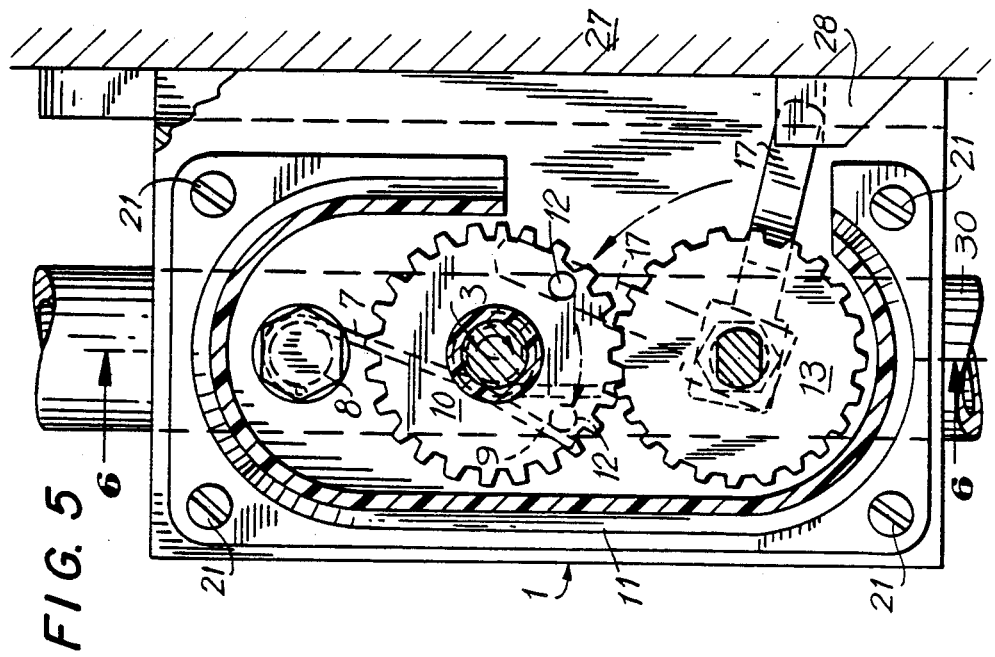

INTRAVENOUS POLE CLAMP

FIELD OF THE INVENTION

This invention pertains to an improved intravenous pole clamp having a locking mechanism. More particularly, it pertains to an intravenous locking pole clamp employing a spring clutch assembly.

BACKGROUND OF THE INVENTION

In the past, intravenous pole clamps have had no need for a locking feature. Security against theft or tampering was not considered to be a significant design consideration. Therefore, medical devices such as a pump simply contained a clamping mechanism, typically a screw thread/knob/bracket arrangement, for attaching to a pole. As new therapies have developed, such as patient controlled analgesia which uses narcotic analgesics, the need for increased security has arisen.

Some prior art patents disclosing I-V pole clamps include Design Pat. No. 269,156 (Slinkard) which discloses an I-V pole clamp with conventional means for securing to an I-V pole. U.S. Pat. No. 4,586,691 (Koslow) discloses a clamp for regulating the flow from an I-V bottle tube. U.S. Pat. No. 4,572,536 (Doughty) discloses a device for coupling an I-V pole to a wheelchair.

Other I-V pole clamps used in the field include those in which the medical device such as a pump is permanently affixed to the pole. It can only be removed by partially disassembling of the pole or the pump. User versatility and convenience is not available with this type system. Other contemporary systems include an I-V pole clamp that locks to a pole but uses a rachet mechanism rather than a spring clutch. With such a system, the knob used to tighten the mechanism to the pole can be rotated backwards up to one "ratchet tooth". This may result in loosening or even removal from certain poles. In such systems the pole mounting mechanism is permanently part of the pump. With such a system, not only must the user properly position the pole clamp, but the large, heavy pump must be simultaneously aligned and supported. Further, during transport of the medical device, the pole mounting mechanism must be carried as well.

Spring clutches are a design element which have been used for a number of applications in the past. U.S. Pat. No. 4,321,992 (Gallo) relates to a wrap spring clutch coupling. However, the Gallo clutch is directed to coupling two hubs and does not disclose either the clutch element of the present invention or application to an I-V pole clamp.

SUMMARY OF THE INVENTION

The present invention provides, for the first time, an I-V pole clamp employing a spring clutch as a locking mechanism. A gear/pin arrangement concentric to a threaded stud restrains the wrap spring clutch in an unlocked position and may be easily moved to a locked position using a key. A dove tail mounting system on the clamp body conveniently matingly mounts a medical device such as a pump. An interlocking lever actuated by the spring clutch locks the medical device to the clamp. In addition, a threaded stud threadingly inserted through the clamp body to lock the clamp to the I-V pole includes a rotating disk at its forward end to contact the I-V pole to reduce friction at contact and to minimize damage to the pole.

It is an object of the present invention to provide an I-V pole clamp which can be locked to a pole or other suitable mounting structure so that theft or tampering with the medical device affixed thereto is discouraged.

It is another object to provide a locking pole clamp which can be easily unlocked for transport or repositioning. It is a further object to provide a locking pole clamp for a medical device such that the device may be removed from the pole clamp when unlocked.

It is a still further object to provide an improved pole clamping mechanism which cannot be loosened, even slightly, from the pole when locked.

The disclosed invention provides a construction having concentric locking/unlocking actuator gearing, allowing ease of assembly, simplicity of design, a wide range of proper adjustment positions, wide tolerances on component parts, and immunity to changes or distortion with excess use or abuse. In addition, the pole clamp will accommodate a number of pole sizes and shapes as well as other suitable structures such as bed rails and head boards.

These and other objects and advantages will be evidenced from the detailed description which follows which is to be read in connection with the drawings.

BRIEF DESCRIPTION OF THE DRAWINGS

FIG. 5 is a view in elevation, partly in cross section and partly in phantom, along section 5—5 of FIG. 4.

FIG. 6 is a cross-sectional view along section 6—6 in FIG. 5.

FIG. 7 shows the wrap spring engaging the stud so as to allow turning in only one direction.

FIG. 8 shows the wrap spring in a position releasing the stud so as to allow turning in both directions.

DETAILED DESCRIPTION OF THE PREFERRED EMBODIMENT

Figure 1:
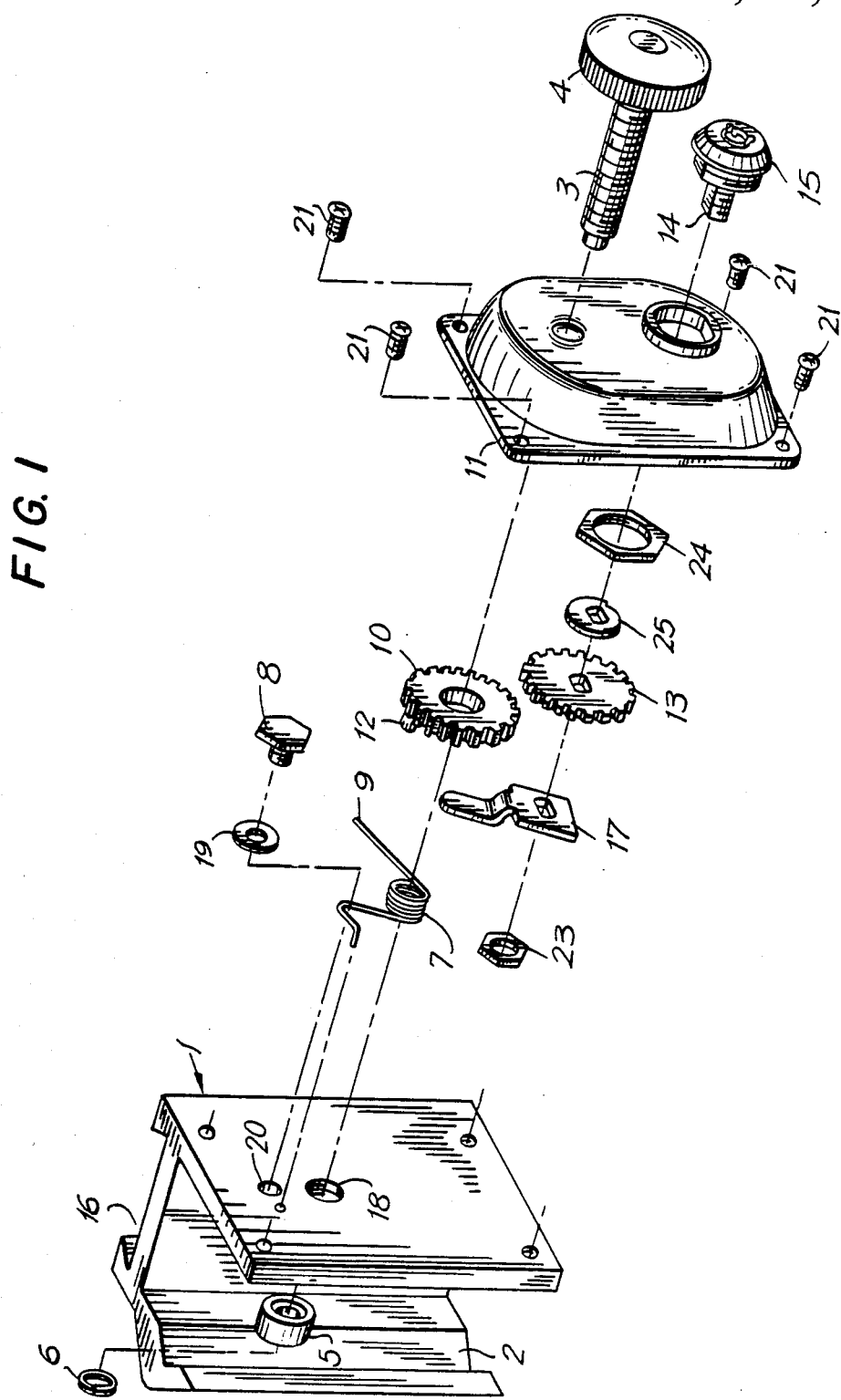
FIG. 1 is an exploded view of the present invention disclosing the parts of the pole clamp in an unassembled condition with dotted lines indicating locations on assembly.

In FIG. 1, clamp body 1 is illustrated. Clamp body 1 is preferably an aluminum extrusion of the shape illustrated in FIG. 1 and adapted to contact I-V poles or other acceptable mounting structures such as bed rails, head boards, or tables. A "V" shaped feature 2 is adapted for use with a round I-V pole 30. However, alternate shapes may be adapted for different mounting structures. The I-V pole 30 or other mounting structure is clamped by threaded stud 3 which advances as it is turned because of its mating interaction with threaded aperture 18 in the clamp body. Threaded stud 3 is turned using knob 4 which is integral with stud 3. Threaded aperture 18 aligns with the "V" of the clamp body for proper centering. A spinning disk 5 is mounted on the end of threaded stud 3 using a push-on type ring 6. The mounting of disk 5 allows it to rotate freely while remaining mounted on the end of threaded stud 3. Spinning disk 5 operates to lower friction forces between the stud 3 and pole 30 during clamping contact to allow more torque to be applied to knob 4 and be transferred into clamping force against the I-V pole 30. It also helps to prevent marring of the I-V pole 30 or other structure being clamped.

A wrap spring 7 with a free state internal diameter less than the diameter of stud 3 is threaded onto stud 3 so that the wrap spring coils interengage with the threads of threaded stud 3. One end of wrap spring 7 is firmly affixed to the clamp body using a holding screw 8. Screw 8 having washer 19 mounted thereon is threadingly engaged to aperture 20 in the clamped body firmly affixing one end of spring 7 thereto. The free end 9 of wrap spring 7 is normally restrained. The spring having one fixed end and a free end 9 movable by stud 12 forms a spring clutch. When the spring's free end 9 is unrestrained and wrap spring 7 is in the one-way clutch mode, the threaded stud can only be advanced. Attempts to withdraw (or unscrew) the stud 3 results in the wrap spring 7 tightly locking via friction forces onto the stud threads thereby preventing the stud 3 from turning. The configuration described above wherein the free end is unrestrained comprises the "locked" position. In this position, the locking pole clamp can be mounted on and tightened to an I-V pole 30, yet cannot be removed.

In accordance with the present invention, to unscrew stud 3 the free end 9 of spring 7 must be unwound slightly so that the internal diameter of wrap spring 7 is greater than the diameter of stud 7. This prevents the spring 7 from tightly coiling and locking around stud 3 when the stud is unscrewed. To accomplish the slight unwinding and restraining, the following system is provided. Gear 10 is mounted on plastic housing 11. The housing 11 has a cylindrical bearing surface on which the gear may rotate. This surface and thus the gear is concentric with threaded stud 3 which passes through gear 10. An actuating pin 12 is integral with gear 10. Pin 12 will engage then slightly unwind and restrain the wrap spring's free end 9 when gear 10 is rotated to the proper position.

Another connecting gear 13 meshes with first gear 10 to rotate gear 10 between the locked (unrestrained wrap spring) and unlocked (restrained wrap spring) position. In turn, this connecting gear 13 is mounted on the lock shaft 14 of lock 15. Lock 15 is rigidly affixed to housing 11. Lock 15 may be locked or unlocked using a key (not shown). Housing 11 serves as an assembly structure as well as a covering to the mechanism to prevent tampering.

Housing 11 is affixed to clamp body 1 by screws 21 inserted into apertures 22 on the clamp body. Rectangular lock shaft 14 rotates gear 13 and interlocking lever 17 when a key is turned in the lock. Nut 23 fastens lock 15 to plastic housing 11. Lock shaft 14 passes through washer 24 and spacer 25. When assembled, housing 11 is mounted flush with clamp body 1 and the elements shown in FIG. 1, located between plastic housing 11 and clamp body 1 are all housed within housing 11.

Figure 2:
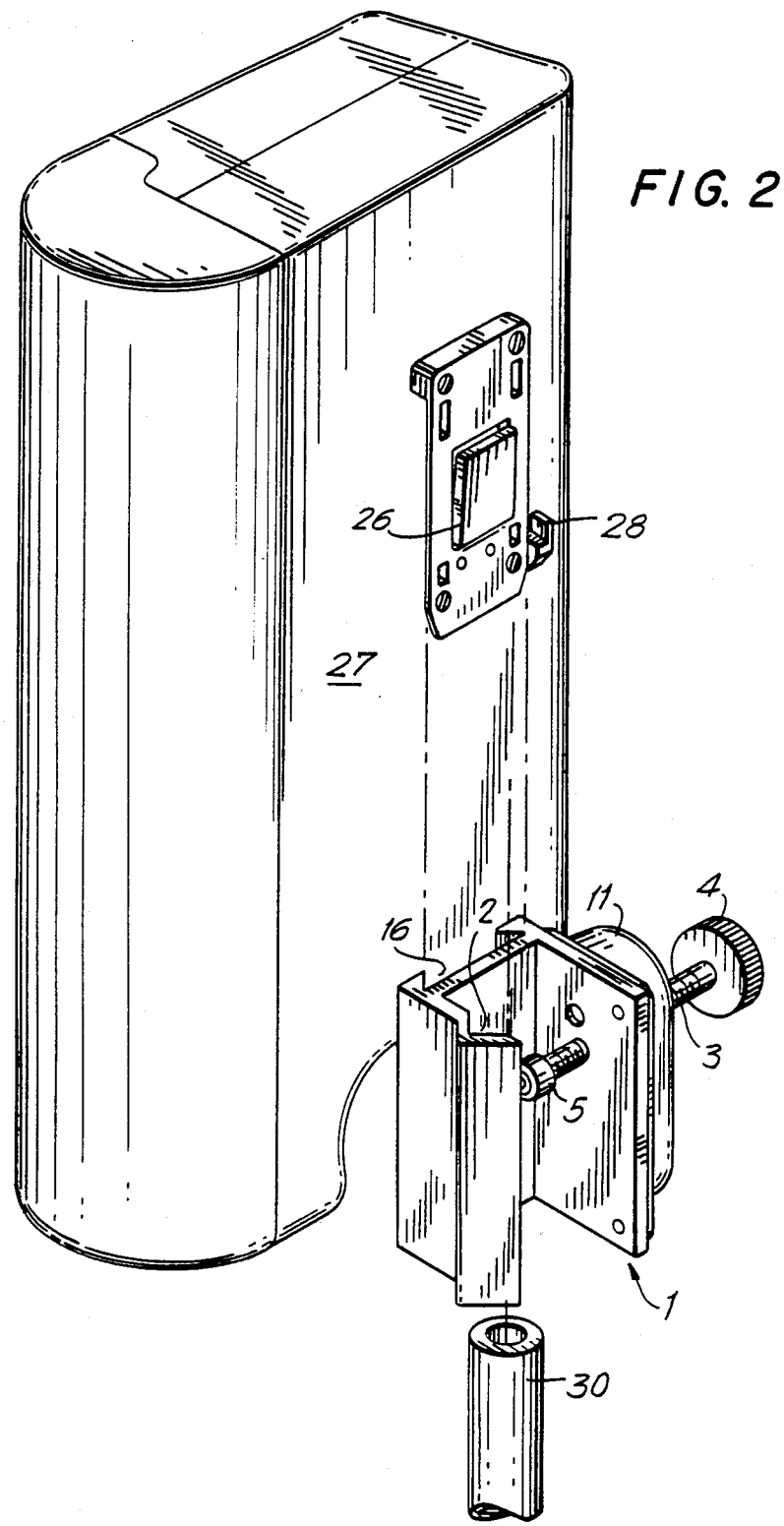
FIG. 2 is a perspective view, partly in elevation, of the pole clamp and the pump which locks thereto.
Figure 3:
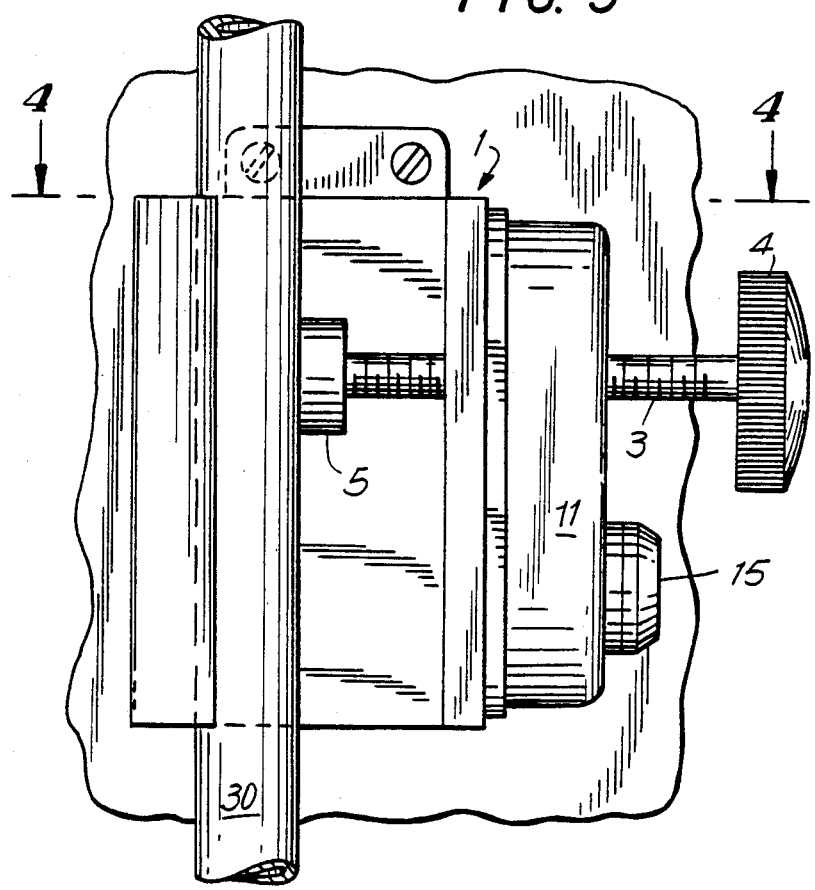
FIG. 3 is a view in elevation of the pole clamp as it is attached to a pole clamp and the pump.
Figure 4:
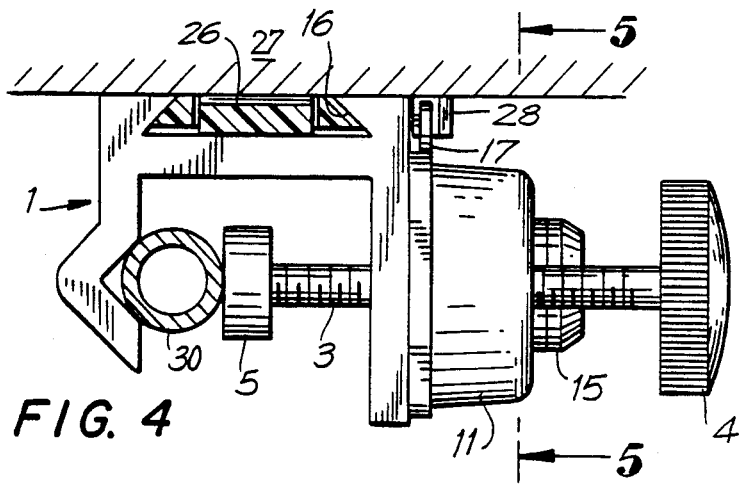
FIG. 4 is a cross-sectional view, partly in elevation along section 4—4, of FIG. 3.

The entire aforementioned assembly can be permanently attached to a medical device. However, the preferred embodiment also includes an additional user convenience. A dove-tail element 16 exists on clamp body 1. A mounting plate 26 such as is disclosed in FIG. 2, which is attached to the medical device 27, such as a PCA pump, has a mating dove-tail feature. The face of the dove tail 26 is of an inclined angle from the medical device 27 so as to restrain the downward vertical movement of medical device 27 when mounted on clamp 1.

Assembly of these two dove-tails 16 and 26 together by the user results in a stable attachment of the medical device 27 to the pole. To lock the medical device 27 to the pole locking clamp 1, an interlocking lever 17 rotates with the connecting gear 13, lock 15, and key (not shown). A protrusion 28 on the medical device 27, adjacent to the dove-tail element 26 on the medical device 27, will engage with the interlocking lever 17 when it is in a locked position thus preventing disassembly of the connected dove-tails 16 and 26. In the unlocked position the dove-tails 16 and 26 are free to slidingly disengage. Nonetheless, the locking I-V pole clamp 1 still remains firmly attached to the pole 30. This allows convenient transport of the medical device 27 and convenient repositioning of the locking I-V pole clamp if desired.

Although a detailed description of the preferred embodiment of the present invention has been provided, it is to be understood that the invention is not limited thereby but is to be determined by the claims which follow.

We claim:

1. An intravenous pole clamp comprising:
   a body having means for attaching to a medical device and a means for attaching to a support element;
   the means for attaching to a support element including a stud threadedly engaging the body and adapted to grip a support pole when tightened;
   a locking means affixed to the body; and
   a spring means acting as a spring clutch mounted on the stud and actuated by the cocking means adapted to allow the stud to rotate inwardly and outwardly when unlocked and to rotate inwardly but not outwardly when locked, the spring means being a wrap spring threaded on the stud having one end fixed to the clamp body and one free end.

2. An intravenous pole clamp according to claim 1 having a housing mounted flush with said body.

3. An intravenous pole clamp according to claim 2 wherein the locking means comprised a lock cylinder, having a lock shaft, affixed to the housing, a first gear connected to the lock shaft and a second gear connected to the stud, the second gear engaging the first gear and having an actuating pin extending therefrom wherein the actuating pin contacts the free end of the wrap spring to unwind it slightly and restrain it when the locking means is in an unlocked position.

4. An intravenous pole clamp according to claim 3 further comprising a spinning disk mounted on the forward end of the stud.

5. An intravenous pole clamp according to claim 3 wherein the means for attaching to a medical device comprising a means for coupling the clamp to a medical device and means for locking the clamp to the medical device.

6. An intravenous pole clamp according to claim 5 wherein the means for coupling to a medical device comprises a dove-tail shaped configuration on one side of the clamp and wherein the means for locking the clamp to a medical device comprises a lever mounted on the shaft of the lock and adapted to interengage with a medical device when locking means is in a locked position.

7. An intravenous pole clamp according to claim 6 wherein the clamp body contains a first wall having a threaded aperture therein, a second wall to which the dove-tail connecting member is attached, a third wall having a V-shaped portion for receiving an I-V pole clamp and one opened side, wherein the V-shaped portion is aligned with the stud.

8. An intravenous pole clamp according to claim 7 wherein the threaded stud has a knob for turning affix thereto.

9. An intravenous pole clamp according to claim 8 wherein rotating the lock shaft rotates the first gear which in turn rotates the second gear which in turn rotates the actuating pin which in turn unwinds and retains the free end of the wrap spring.

* * * * *

UNITED STATES PATENT AND TRADEMARK OFFICE
CERTIFICATE OF CORRECTION

PATENT NO. : 4,844,397
DATED : July 4, 1989
INVENTOR(S) : James G. Skakoon and Thomas Chan It is certified that error appears in the above-identified patent and that said Letters Patent is hereby corrected as shown below:

Column 4, line 32, "cocking" should be --locking--.

Column 4, line 41, "comprised" should be --comprises--.

Column 4, line 62, "lock" should be --locking means--.

Column 4, line 64, after "when" insert --the--.

Column 5, line 5, "affix" should be --affixed--.

Signed and Sealed this

Eleventh Day of December, 1990

Attest:

HARRY F. MANBECK, JR.

*Attesting Officer*       *Commissioner of Patents and Trademarks*